(12) United States Patent
Huh (10) Patent No.: US 9,004,678 B2
(45) Date of Patent: Apr. 14, 2015

(54) SAFETY GLASSES FOR BLOCKING HARMFUL ELECTROMAGNETIC RADIATION AND PREVENTING DAZZLING

(71) Applicant: Otos Wing Co., Ltd., Seoul (KR)

(72) Inventor: moon young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 0 days.

(21) Appl. No.: 14/143,219

(22) Filed: Dec. 30, 2013

(65) Prior Publication Data

US 2014/0204331 A1 Jul. 24, 2014

(30) Foreign Application Priority Data

Jan. 18, 2013 (KR) ........................ 10-2013-0006126

(51) Int. Cl.
| | | |
|---|---|---|
| G02C 7/10 | (2006.01) | |
| G02C 5/12 | (2006.01) | |
| A61F 9/02 | (2006.01) | |
| G02C 3/00 | (2006.01) | |
| G02C 5/04 | (2006.01) | |
| G02C 11/00 | (2006.01) | |

(52) U.S. Cl.
CPC .. *G02C 7/10* (2013.01); *G02C 5/12* (2013.01); *A61F 9/023* (2013.01); *G02C 3/003* (2013.01); *G02C 5/04* (2013.01); *G02C 7/101* (2013.01); *G02C 11/10* (2013.01)

(58) Field of Classification Search
CPC .............. G02C 7/10; G02C 5/12; G02C 1/00; G02C 3/003; G02C 5/04; G02C 7/101; G02C 11/10; G02F 1/1333; G02F 1/1335; G02F 1/13; A61F 9/02; A61F 9/023
USPC ............ 351/44, 136, 137, 158, 159.39, 159.6; 2/432

See application file for complete search history.

(56) References Cited

U.S. PATENT DOCUMENTS

| | | | | |
|---|---|---|---|---|
| 4,756,605 | A * | 7/1988 | Okada et al. ..................... | 349/13 |
| 8,081,262 | B1 * | 12/2011 | Perez .............................. | 349/14 |
| 2008/0062338 | A1 * | 3/2008 | Herzog et al. .................. | 349/13 |
| 2010/0225879 | A1 * | 9/2010 | Pulito ............................ | 351/137 |
| 2012/0204303 | A1 * | 8/2012 | Seo .................................... | 2/12 |

FOREIGN PATENT DOCUMENTS

KR 101285602 7/2013

* cited by examiner

*Primary Examiner* — Scott J Sugarman
*Assistant Examiner* — Wen Huang
(74) *Attorney, Agent, or Firm* — Cantor Colburn LLP (57) ABSTRACT

Disclosed are safety glasses for blocking of harmful electromagnetic radiation and prevention of dazzling which protect eyes from harmful electromagnetic radiation and are ergonomically balanced by arranging the lens portion at the front and the adjuster and battery at the rear side of the temple to ensure convenient wearing of the glasses. The safety glasses include an inner/outer hosing formed of a soft material to closely contact the face of the user and fabricated through double injection molding, thereby ensuring convenient wearing of the glasses.

10 Claims, 11 Drawing Sheets

SAFETY GLASSES FOR BLOCKING HARMFUL ELECTROMAGNETIC RADIATION AND PREVENTING DAZZLING

BACKGROUND OF THE INVENTION

1. Field of the Invention

The present invention relates to safety glasses for blocking of harmful electromagnetic radiation and prevention of dazzling which protect eyes from harmful electromagnetic radiation, ergonomically balance the weight thereof with lenses arranged at the front and an adjuster and a battery arranged at the rear portion of a temple to ensure convenient wearability of the glasses, have an outer housing formed of a soft material to closely contact the face of a user to provide user convenience and an inner housing formed of a hard material, fabricated through double injection molding, allow adjustment of the distance between a Liquid Crystal Display lens ("LCD lens") and eyes, and are comfortably wearable according to the face shape and the height of the nose.

2. Description of the Related Art

Generally, a pair of safety glasses for blocking of harmful electromagnetic radiation and prevention of dazzling, which serves to protect a user from harmful electromagnetic radiation, are used to protect eyes from harmful electromagnetic radiation generated in welding and medical laser operations. Such safety glasses are configured such that an LCD lens blocks harmful electromagnetic radiation when the electromagnetic radiation is sensed through an optical sensor. The LCD lens, which is transparent in normal times, is darkened to block harmful electromagnetic radiation when the electromagnetic radiation is generated.

However, such safety glasses for blocking of harmful electromagnetic radiation require a battery and a controller to delay opening operation in addition to an optical sensor and an LCD lens. Accordingly, it is difficult to design the safety glasses in the shape of normal eyeglasses. Further, when safety glasses for blocking of harmful electromagnetic radiation in the shape of normal eyeglasses are worn, the fixed nose support may not properly fit to the face shape and nose height of a user, causing inconvenience. Particularly, in the case that the user is wearing a pair of eyeglasses for vision correction, the safety glasses for blocking of harmful electromagnetic radiation need to be worn and placed in front of the eyeglasses in an overlapping manner. In this case, the safety glasses for blocking of harmful electromagnetic radiation are spaced from the face and thereby gaps are created between the safety glasses and the face at the lower side and lateral sides of the safety glasses. Accordingly, the safety glasses may not safely block harmful electromagnetic radiation.

In addition, a conventional technology (Korean Patent No. 10-1285602) has a lens, and a controller and a battery all arranged at the front, causing the center of mass to be positioned farther to the front. Particularly, the weight of the product requires a pressure band to be used to ensure close contact such that the glasses are securely held on the head of the user. Thereby, the user may experience inconvenience in wearing the glasses. In addition, when the glasses are worn for a long time, fatigue increases due to the applied pressure.

CITED REFERENCE

Patent Document

Korean Patent No. 10-1285602 (Jul. 8, 2013)

SUMMARY OF THE INVENTION

Therefore, the present invention has been made in view of the above problems, and it is an object of the present invention to provide ergonomic safety glasses for blocking of harmful electromagnetic radiation and prevention of dazzling which are designed in the shape of eyeglasses and distribute the weight thereof as wide as possible to provide a user with the sensation of wearing normal eyeglasses.

It is another object of the present invention to provide safety glasses for blocking of harmful electromagnetic radiation and prevention of dazzling which are capable of protecting eyes from very strong visible light generated in medical procedures.

It is another object of the present invention to provide safety glasses for blocking of harmful electromagnetic radiation and prevention of dazzling which may be conveniently worn to perform welding.

It is another object of the present invention to provide safety glasses which may form an internal seating space and prevent creation of gaps at the lower side and lateral sides of the glasses even when worn and placed in front of a pair of eyeglasses for vision protection.

It is another object of the present invention to provide safety glasses for blocking of harmful electromagnetic radiation that allow adjustment of a nose support.

It is a further object of the present invention to provide safety glasses for blocking of harmful electromagnetic radiation and prevention of dazzling which are provided with a lateral surface protection frame having a soft outer housing for close contact with the face of a user and a hard inner housing for convenient attachment and detachment formed through double injection molding.

In accordance with the present invention, the above and other objects can be accomplished by the provision of safety glasses for blocking of harmful electromagnetic radiation including a pair of LCD lenses for blocking of harmful electromagnetic radiation, a glasses frame adapted to be worn on a face of a user with the LCD lenses fitted to the left and right sides thereof, the glasses frame being provided with an edge protruding rearward to closely contact the face and an optical sensor for sensing of harmful electromagnetic radiation installed between the LCD lenses, and a temple adapted to be hung on ears and joined to both sides of the glasses frame, one side end of the temple being provided with a power supply unit for mounting of a battery and the other side end of the temple being provided with a control switch unit.

The control switch unit may be configured to control a remaining battery charge indication lamp, a welding mode, a cutting/grinding mode, and a sensitivity to select and perform welding or cutting/grinding.

The glasses frame may include a front frame and a rear frame, the LCD lenses being fitted between the front frame and the rear frame and an optical sensor being accommodated and mounted between the front frame and the rear frame, wherein a sensing hole allowing the optical sensor to sense the harmful electromagnetic radiation therethrough may be formed at a center of the front frame, and an edge of the front frame protrudes rearward, and the rear frame may be accommodated in and fastened to an interior of the edge of the front frame, and both sides of a lower portion of a nose support are joined to a center of the rear frame.

The nose support may be provided with an elastic segment having a guide protrusion formed at one side of each of the ends protruding forward from both sides of the elastic segment, and the rear frame may be provided with a guide groove to guide movement of the guide protrusion fitted thereinto.

The safety glasses may further include an auxiliary frame coupled to the glasses frame and extending from a lower side and lateral sides of the protruding edge of the glasses frame to cover the edge. The glasses may further include a lateral surface protection frame having an outer housing formed of a soft material to closely contact the face of the user and fabricated through double injection molding.

The power supply unit may be provided with the battery having a coin shape and a battery cover having a hinge, and the safety glasses may be one of medical safety glasses, industrial safety glasses, sport goggle, sunglasses, and fashion glasses.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Reference will now be made in detail to the embodiments of the present invention, examples of which are illustrated in the accompanying drawings.

As shown in FIGS. 1 to 13, the safety glasses for blocking of harmful electromagnetic radiation include a pair of LCD lenses for blocking of harmful electromagnetic radiation, a glasses frame 200 adapted to be worn on the face with the LCD lenses fitted to the left and right sides thereof and provided with an edge protruding rearward to closely contact the face and an optical sensor 210 for sensing of harmful electromagnetic radiation installed between the LCD lenses, and a temple 300 adapted to be hung on ears and joined to both sides of the glasses frame, one side end of the temple being provided with a power supply unit 310 for mounting of a battery and the other side end of the temple being provided with a control switch unit 320. A circuit wire is installed in the temple to connect the power supply unit 310 to the control switch unit 320. The weight of the safety glasses is distributed to the front portion having the LCD lenses 100 and the rear portion having the battery and the control switch unit 320 including a controller such that the safety glasses are balanced when worn by the user.

Figure 1:
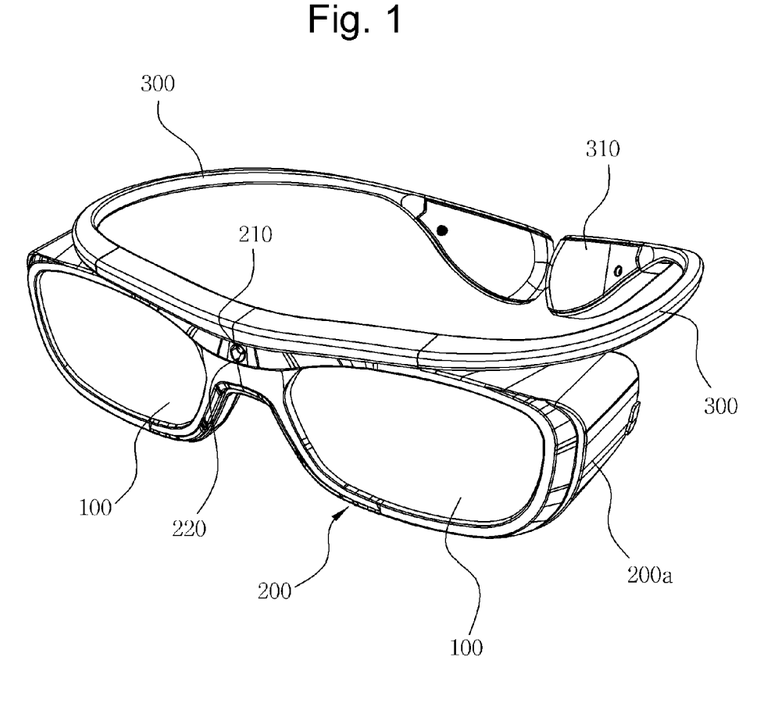
FIG. 1 is a perspective view illustrating safety glasses for blocking of harmful electromagnetic radiation and prevention of dazzling.
Figure 2:
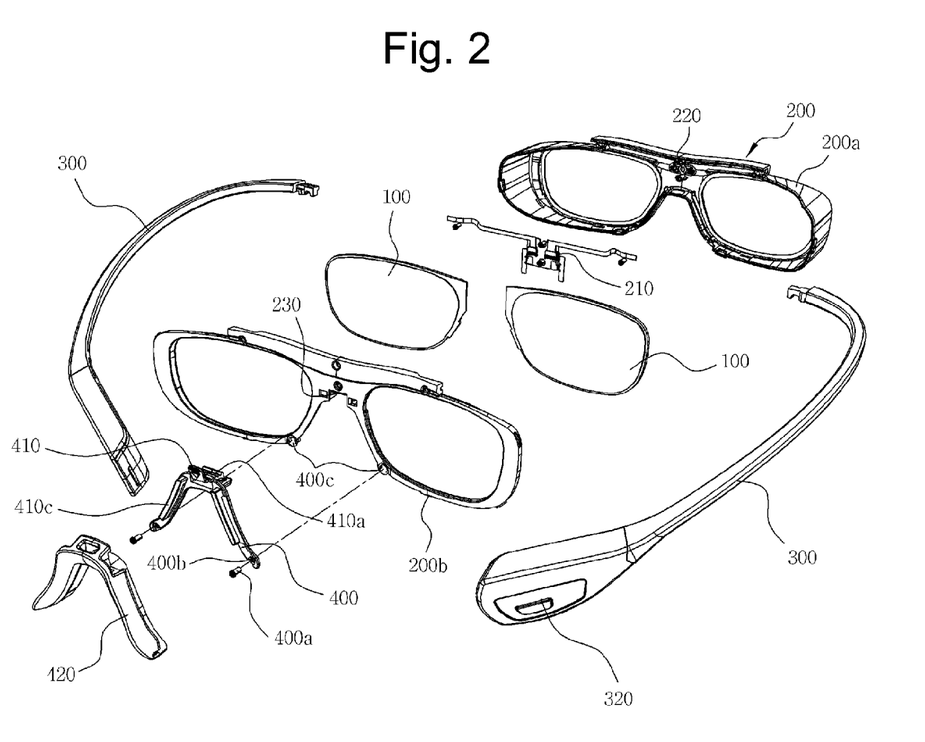
FIG. 2 is an exploded perspective view illustrating safety glasses for blocking of harmful electromagnetic radiation and prevention of dazzling according to one embodiment of the present invention.
Figure 3:
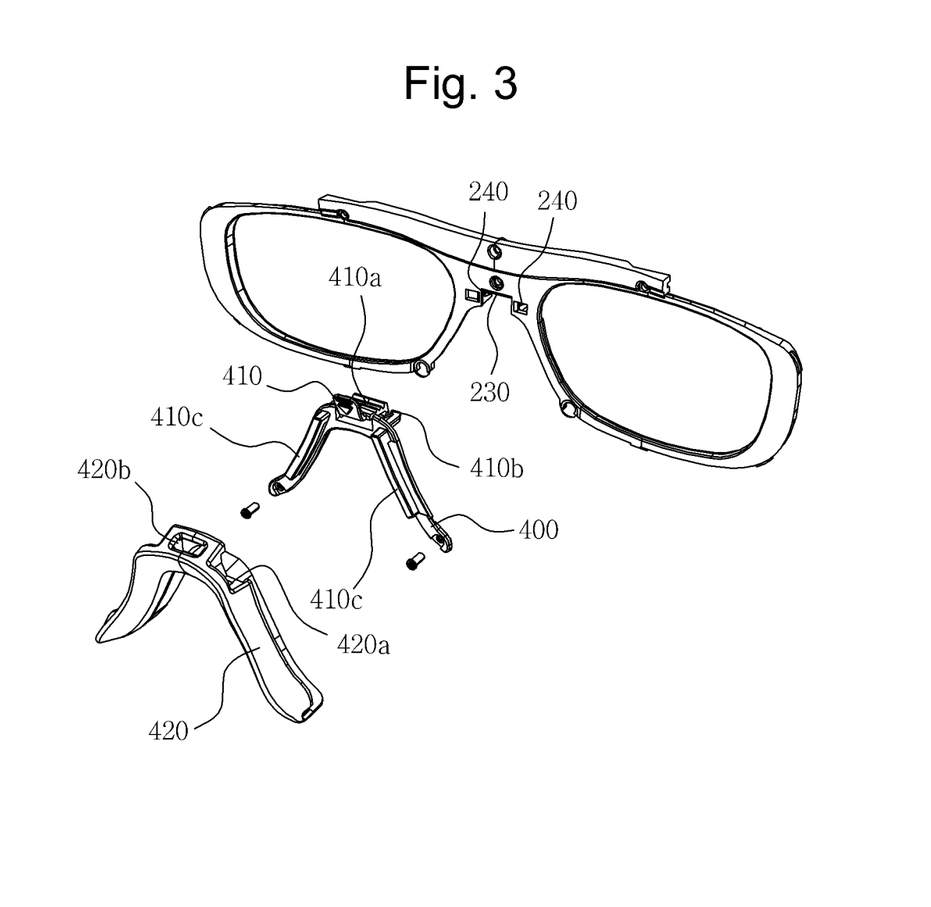
FIGS. 3 and 4 are exploded perspective views illustrating a recessed portion of the safety glasses according to one embodiment of the present invention.

The LCD lenses 100 serve to block harmful electromagnetic radiation directed to eyes and is configured with a pair of left and right LCD lenses. The LCD lenses 100 remain transparent when harmful electromagnetic radiation is not present, and are darkened to protect the eyes of the user when the harmful electromagnetic radiation is emitted. As shown in FIGS. 2 and 3, the LCD lenses 100 are connected to a circuit board when they are coupled to the glasses frame 200. Thereby, the LCD lenses 100 are controlled by the optical sensor 210 and the control switch unit 320, which will be described later.

The glasses frame 200 is worn on the face of the user with the LCD lenses 100 fitted to the left and right sides of the glasses frame. The edge of the glasses frame 200 protrudes rearward to closely contact the face, and the optical sensor 210 for sensing harmful electromagnetic radiation is installed between the left and right LCD lenses 100. That is, the glasses frame 200 controls operation of the LCD lenses 100 by sensing harmful electromagnetic radiation through the optical sensor 210 at the front center of the glasses frame 200, and closely contact the face to prevent harmful electromagnetic radiation from reaching the eyes through the lateral side or lower sides of the glasses frame 200.

In one embodiment illustrated in FIGS. 2 and 3, the glasses frame 200 includes a front frame 200a and a rear frame 200b. The front frame 200a and the rear frame 200b allow the edges of the LCD lenses 100 to be fitted therebetween, and accommodate the optical sensor 210 therebetween. Herein, a sensing hole 220 through which the optical sensor 210 senses harmful electromagnetic radiation is formed at the center of the front frame 200a, and the edge of the front frame 200a protrudes rearward. The rear frame 200b is accommodated in and fastened to the interior of the edge of the front frame 200a. Both sides of the lower portion of the nose support 400 are joined to the center of the rear frame 200b.

Meanwhile, inclination of the nose support is adjusted according to introduction and withdrawal of an elastic segment 410 of the nose support 400, which will be described later, through the rear frame 200b of the glasses frame 200. A step 230 is formed at the lower center of the rear frame 200b to interrupt the interruption step 410a such that the inclination is adjusted. Through holes 400b are formed at both sides of the lower portion of the nose support 400 to fix both sides. Fixing pieces 400a are installed in through holes 400b. The fixing pieces are installed in and fixed to installation holes 400c of the rear frame 200b. In addition, guide grooves 420a to guide movement guide protrusions 410b of the nose support 400 fitted thereinto are formed at the front of both sides of the step 230 of the rear frame 200b.

The temple 300 is joined to both sides of the glasses frame 200 and hung on ears of the user. The power supply unit 310 for mounting of the battery is formed at one side end of the temple 300, and the control switch unit 320 is installed at the other side end of the temple 300. That is, as shown in the figures, the temple 300 is configured with a pair of left and right temples and is joined to both sides of the glasses frame. The power supply unit and the control switch unit are connected to the LCD lenses and the optical sensor in a circuit through the interior of the temple 300.

Figure 5:
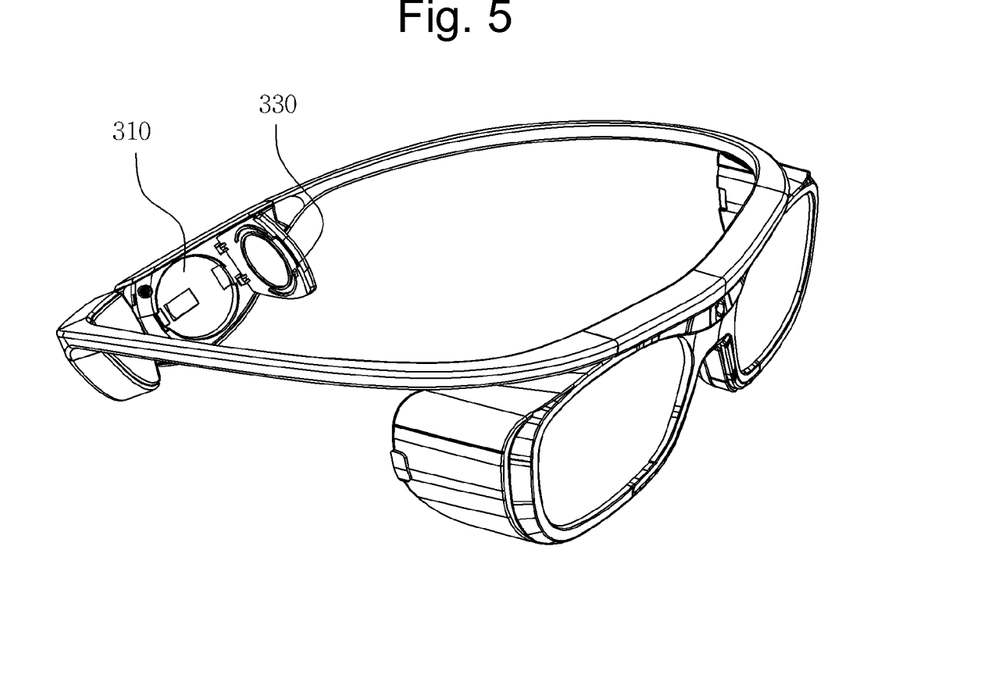
FIG. 5 is a perspective view illustrating a power supply unit at an opened position.
Figure 6:
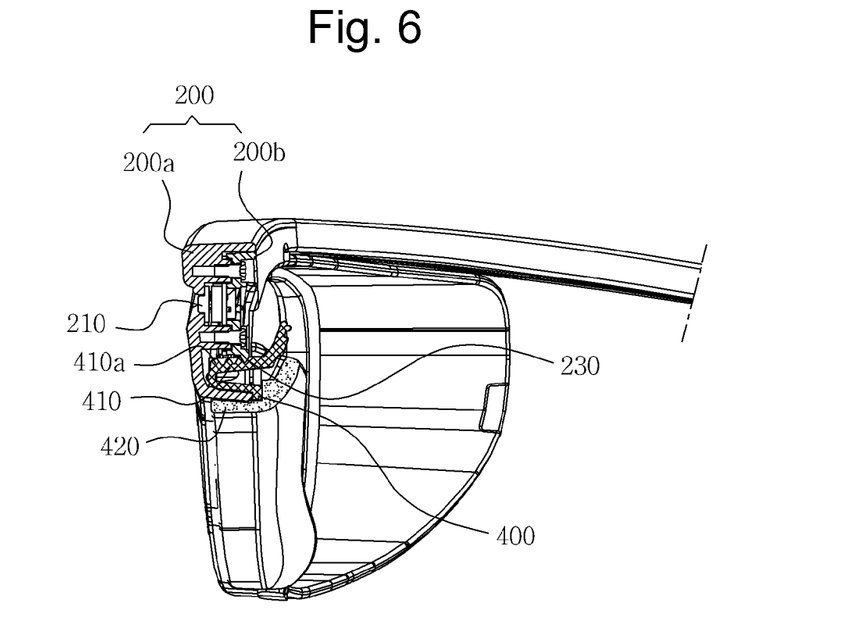
FIGS. 6 and 7 are cross-sectional views illustrating a nose support of the safety glasses for blocking of harmful electromagnetic radiation and prevention of dazzling according to one embodiment of the present invention.
Figure 7:
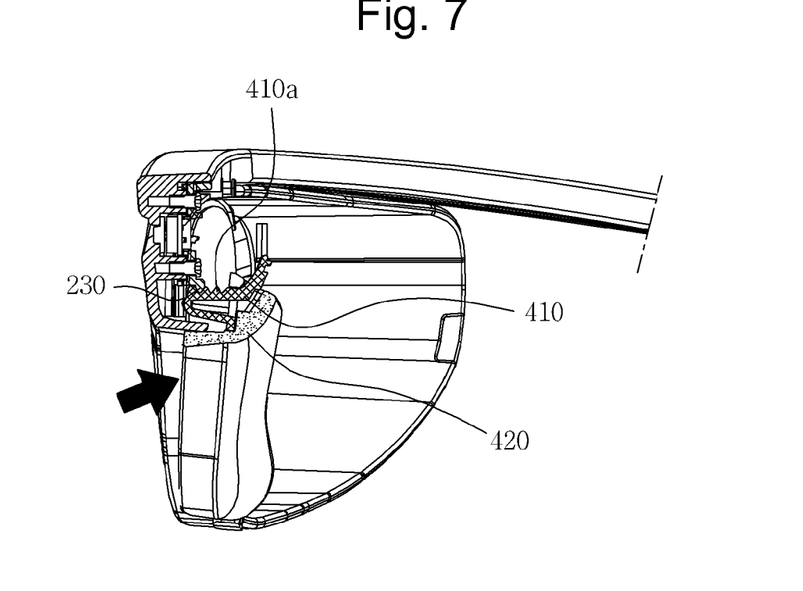
Figure 8:
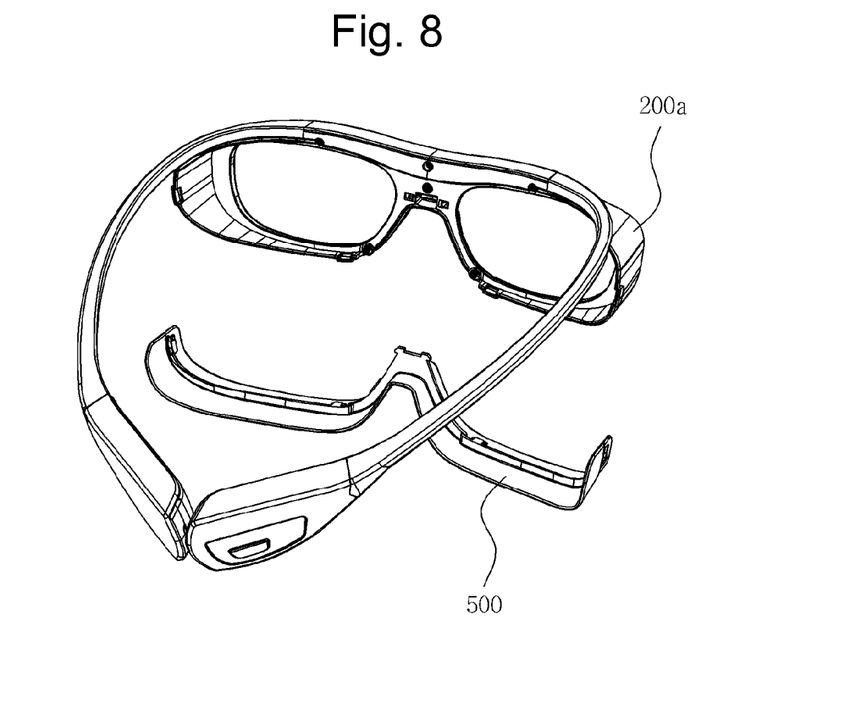
FIG. 8 is a view illustrating joining of an auxiliary frame to the safety glasses for blocking of harmful electromagnetic radiation according to one embodiment.
Figure 9:
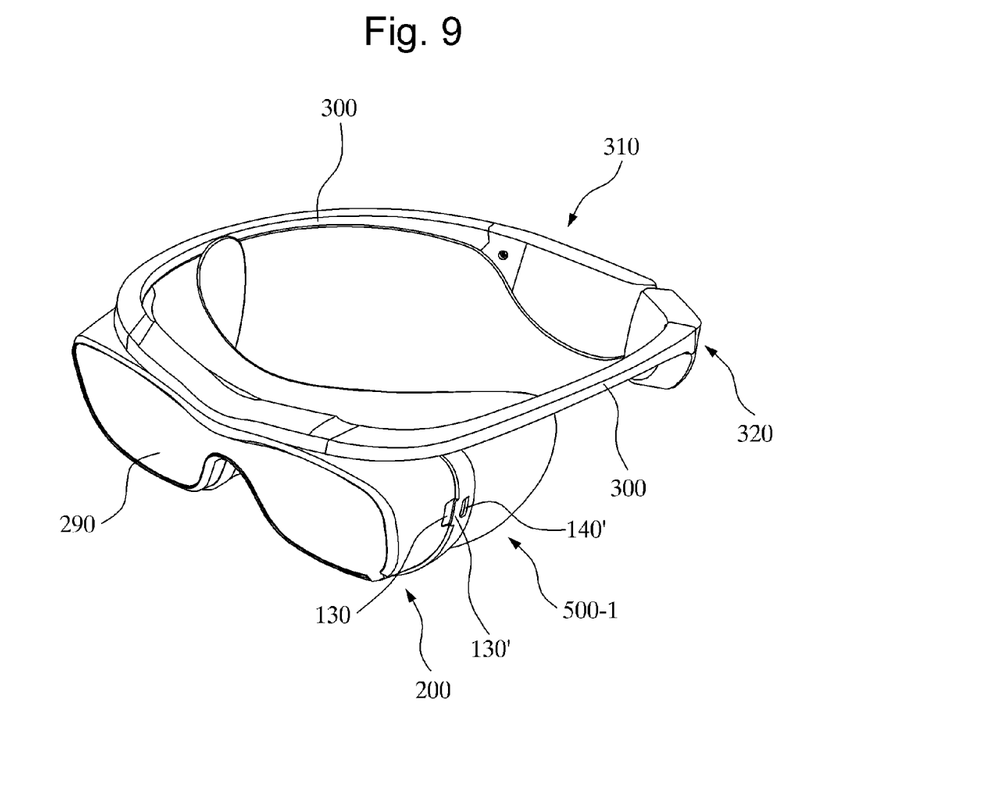
FIG. 9 is a perspective view illustrating safety glasses for blocking of harmful electromagnetic radiation and prevention of dazzling applied to work such as welding, and cutting/grinding according to another embodiment of the present invention.

As shown in FIG. 5, a battery cover 330 provided with a hinge facilitating replacement of the battery having a coin shape is mounted to the power supply unit 310. Thereby, the power supply unit 310 prevents the battery cover from being separated when the cover is opened. The control switch unit 320 turns the LCD lenses 100 on/off and the optical sensor 210 operated by the power supply unit 310. If necessary, the power supply unit and the control switch unit installed on the left and right sides may be interchanged.

The nose support 400 is joined to the center of the rear portion of the glasses frame 200 and worn on the nose in a manner that it is supported by the nose. Both sides of the lower portion of the nose support 400 are joined to both sides of the glasses frame 200. The portion of the nose support 400 is inclined at an adjustable angle with respect to the glasses frame 200. That is, with the edge of the glasses frame 200 in close contact with the face of the user, inclination of the nose support 400 is adjusted according to the height of the nose of the user such that the glasses frame 200 does not move down and the glasses are conveniently worn. In one embodiment illustrated in FIGS. 3 and 4, an elastic segment 410 protruding forward and curved to an upper rear side is formed at the upper portion of the nose support 400, and a multi-stepped interruption step 410a is formed on the curved upper surface of the elastic segment in a front-to-back direction. A step 230 is formed at the lower end of the central connection part of the rear frame 200b of the glasses frame 200 such that the interruption step 410a is caught by the step 230. According to the configuration as above, when the upper portion of the nose support 400 is moved back and forth with the elastic segment 410 kept pressed and then released, a groove in the interruption step 410a is caught and fixed by the step 230. Thereby, inclination of the nose support 400 and the cushion cover 420, which is formed of silicone or rubber, is easily adjusted, ensuring convenient wearing of the glasses.

Figure 4:
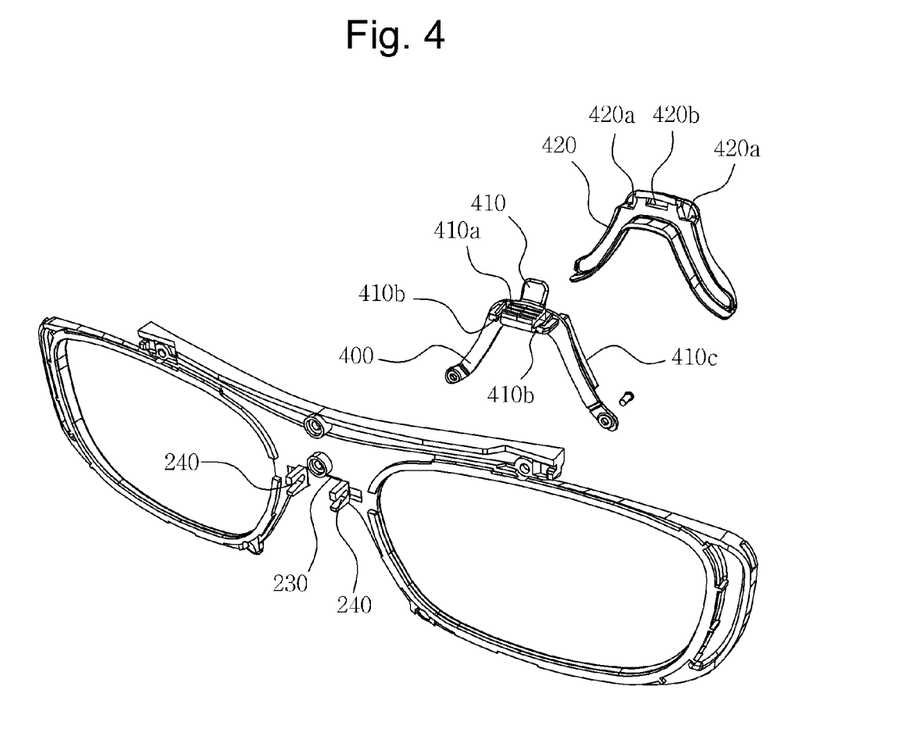

As shown in FIGS. 3 and 4, a guide protrusion 410b is formed at one side of each of the ends protruding forward from both sides of the elastic segment 410. The guide protrusions 410b are movably fitted into guide grooves 240 of the rear frame 200b. In addition, fitting protrusions 410c protruding rearward and having an inverted L shape are formed at both sides of the rear portion of the nose support 400. Fitting holes 420a to press-fit the fitting protrusions 410c thereinto to fix the fitting protrusions 410c are formed at both sides of the cushion cover 420. In addition, a push hole 420b is formed in the upper portion of the cushion cover 420 such that an end of the elastic segment 410 is fitted into the push hole 420b and exposed to the outside to be pushed by hand. Accordingly, the cushion cover 420 is easily and safely fitted into the rear portion of the nose support 400, while inclination of the nose support 400 is easily adjusted using the elastic segment 410. According to one embodiment, the safety glasses include an auxiliary frame 500 coupled to the glasses frame 200 and extending to the lower side and lateral sides of the protruding edge of the glasses frame 200 to cover the edge. That is, in the case that a user wears a pair of eyeglasses for vision correction, the auxiliary frame 500 serves to close the gap between the edge of the glasses frame 200 and the face created by the thickness of the eye. By providing a protrusion and a groove to the glasses frame 200 and the auxiliary frame 500, the glasses frame 200 is easily fitted into and separate from the auxiliary frame 500.

In the case that the auxiliary frame 500 is coupled to the glasses frame 200, the nose support 400 is unnecessary and thus may be removed and stored. According to this embodiment, by designing the nose support 400 to fit to the shape of the glasses and to be adjustable, wearability of the glasses may be enhanced. In addition, since the auxiliary frame 500 closes the gap between the safety glasses and the face created by the eyeglasses for vision correction behind the safety glasses, the user is allowed to use the safety glasses safely and conveniently.

According to another embodiment illustrated in FIGS. 9 to 13, the safety glasses may be used for such operations as welding, cutting and grinding.

The safety glasses according to this embodiment include a pair of LCD lenses 100 for blocking of harmful electromagnetic radiation, a glasses frame 200 adapted to be worn on the face with the LCD lenses 100 fitted to the left and right sides thereof and provided with an edge protruding rearward to closely contact the face and an optical sensor 210 for sensing of harmful electromagnetic radiation installed between the LCD lenses, and a temple 300 adapted to be hung on ears and joined to both sides of the glasses frame, one side end of the temple being provided with a power supply unit 310 for mounting of a battery and the other side end of the temple being provided with a control switch unit 320. A circuit wire is installed in the temple to connect the power supply unit 310 to the control switch unit 320. The weight of the safety glasses is distributed to the front portion having the LCD lenses 100 and the rear portion having the battery and the control switch unit 320 including a controller, thus being balanced when worn by the user.

The battery is inserted into the power supply unit 310 and the control switch unit 320 is provided with switches allowing selection of one of welding and cutting/grinding. The power supply unit 310 may be installed on one of the left and right sides of the temple 300. In this embodiment, a power supply unit having a battery inserted thereinto is formed on the right side of the temple to supply power as shown in the figures. In addition, a remaining battery charge indication lamp 280 is provided to inform of the remaining charge of the battery.

Figure 11:
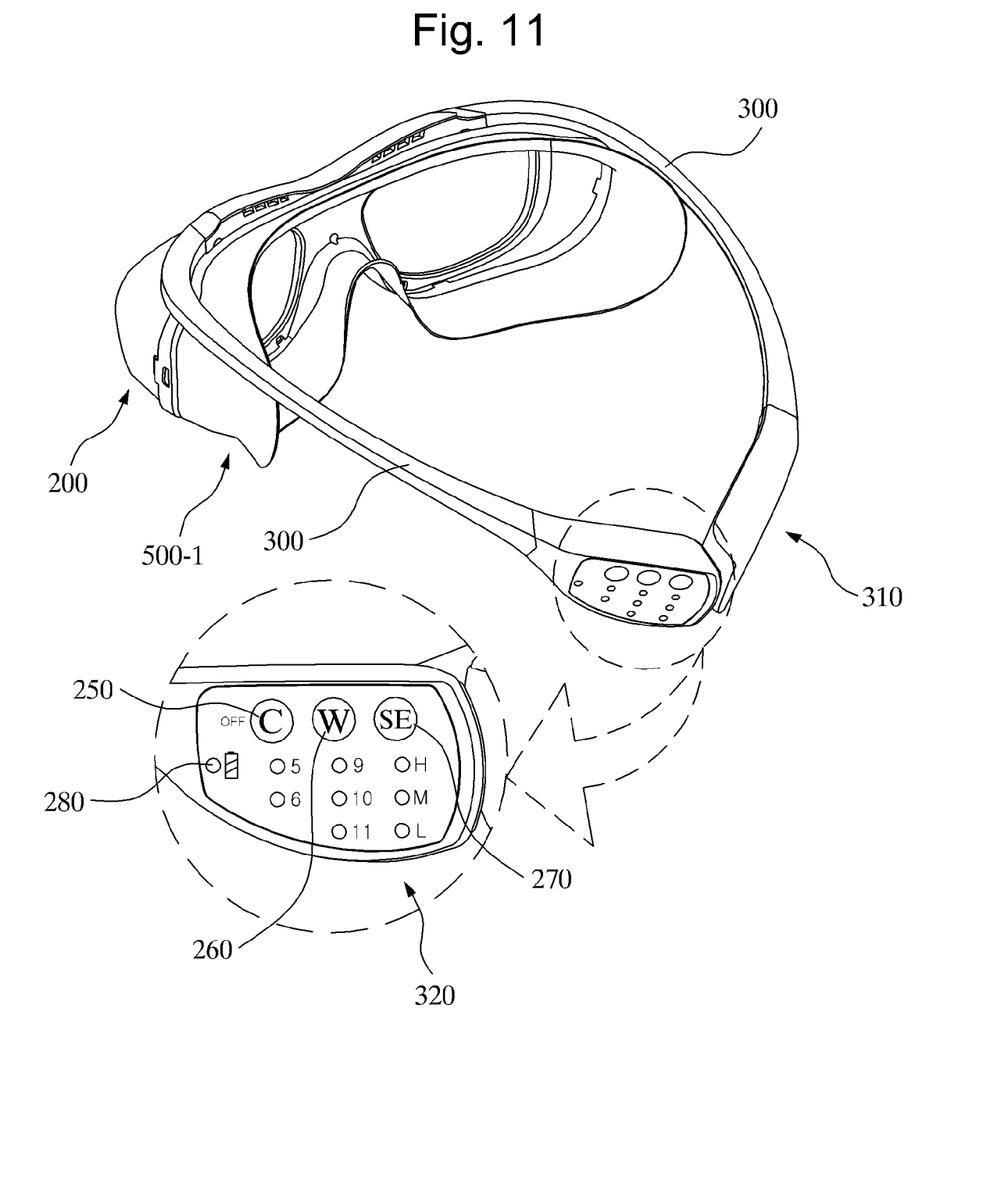
FIG. 11 is an enlarged view illustrating a control switch unit of safety glasses for blocking of harmful electromagnetic radiation and prevention of dazzling according to one embodiment of the present invention.

According to this embodiment, power is turned on when one of the arranged buttons is pressed. When welding needs to be performed, a welding switch 260 (indicated by W) is pressed and then a desired darkening level (level 9, level 10, or level 11) is selected. When cutting/grinding is needed, a cutting/grinding switch 250 (indicated by C) is pressed and a desired degree of darkening (stage 5 or stage 6) of the LCD lenses is selected. In addition, a sensitivity switch 270 (indicted by SE) to adjust a sensitivity of response to the light intensity on the work site or for an intended operation is provided to control darkening of the LCD lenses. Using the sensitivity switch 270, a level of sensitivity is selected from high (H), middle (M) and low (L) levels according to a work environment.

According to this embodiment, light from welding (harmful electromagnetic radiation) is detected through an input signal from the optical sensor 210. Particularly, light produced in welding or cutting is detected by the optical sensor, and sensitivity is set with the sensitivity switch 270 (indicted by SE) to control darkening of the LCD lenses according to the sensitivity of response.

Darkening the LCD lenses to protect worker performing welding or cutting and prevent dazzling is already introduced in the conventional art, and thus a description thereof will be omitted.

Figure 10:
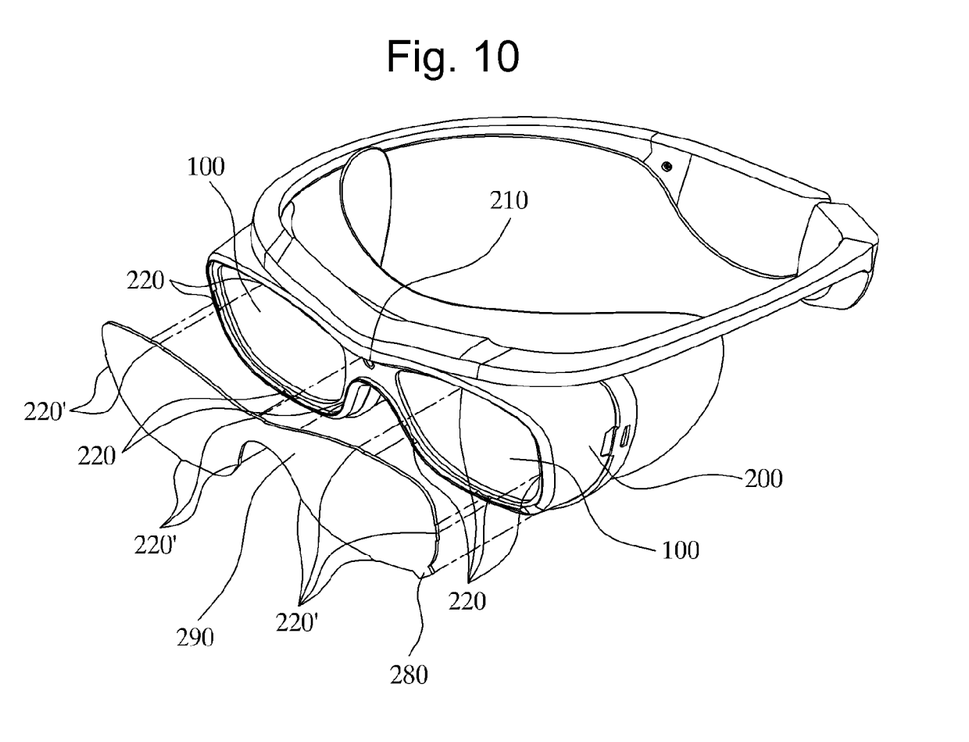
FIG. 10 is a perspective view illustrating coupling of a transparent cover.

According to this embodiment, a transparent cover 290 provided with a projecting protrusion 220' and an escape protrusion 280 formed on the lateral surface thereof to facilitate installation and detachment of the transparent cover 290 is mounted to the front of the LCD lenses 100 for blocking of harmful electromagnetic radiation to protect the lenses from damage.

The transparent cover 290 is formed by stacking a single protection film or plural protection films such that the films may be removed one by one. Thereby, when a film is damaged, it may be immediately removed to perform intended operation. In the embodiment illustrated in FIGS. 12 and 13, the glasses frame 300 includes a front frame 200a and a rear frame 200b.

Figure 12:
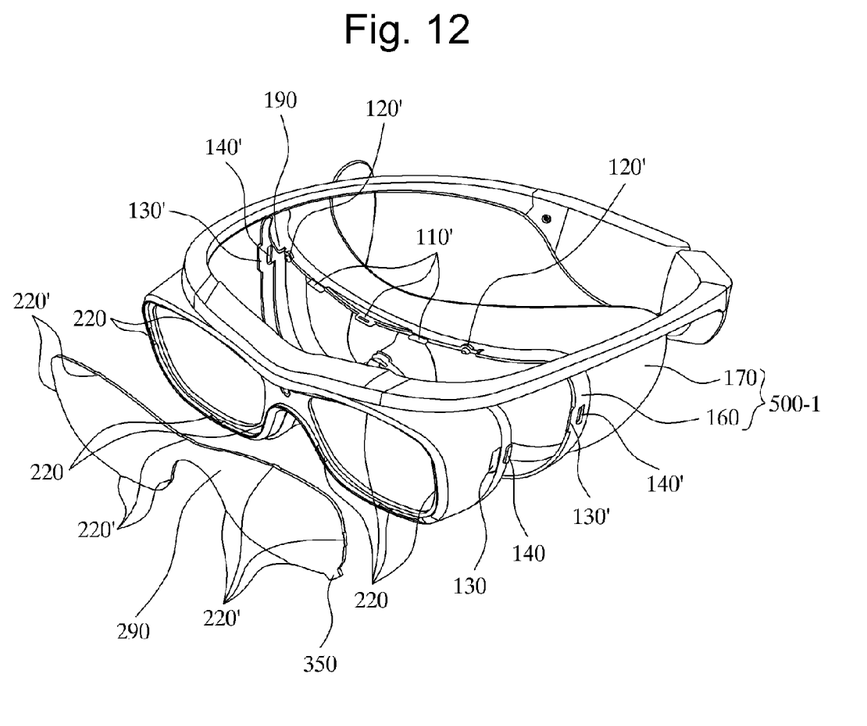
FIGS. 12 and 13 are exploded perspective views illustrating safety glasses for blocking of harmful electromagnetic radiation and prevention of dazzling according to one embodiment of the present invention.
Figure 13:
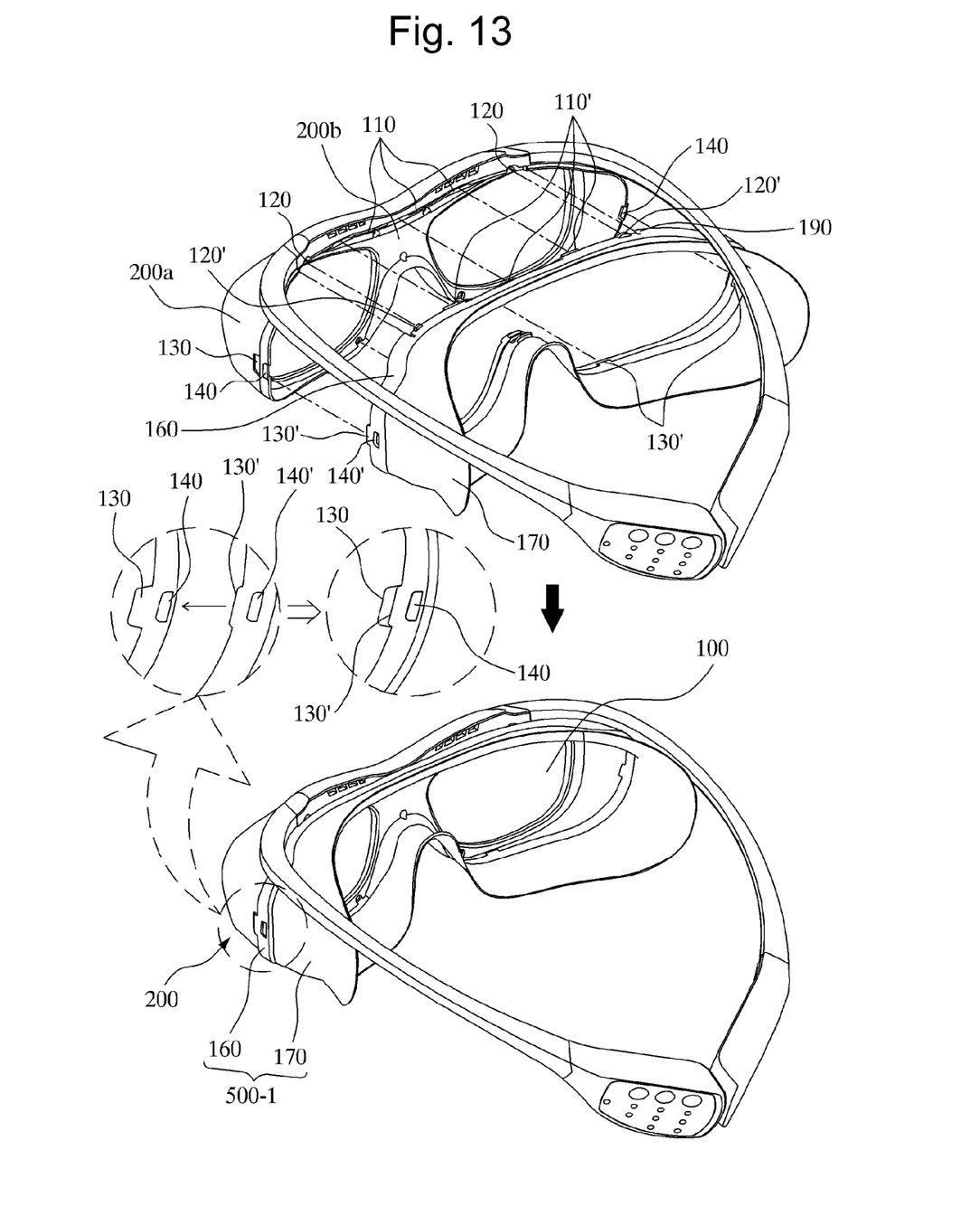

A plurality of fitting grooves 110 is formed at the center of the rear frame 200b, and fitting grooves 120 are provided in the lateral surface on both left and right sides of the center of the rear frame 200b. In addition, central fitting protrusions 110' are formed at the upper center and side fitting protrusions 120' are formed on both sides of the upper center. Thereby, the fitting protrusions are fitted to the fitting grooves. A wing surface 190 is formed to surround the lateral surface of the front frame 200a. A plurality of escape protrusions 130' and fastening holes 140' is formed on the lateral surface of the wing surface 190 to be coupled to the escape grooves 130 and fastening protrusions 140 formed at the front frame. By pulling the escape protrusions 130', the escape protrusions 130' and fastening holes 140' are decoupled from the escape grooves 130 and fastening protrusions 140.

The inner housing 160 provided with the escape protrusions 130' and the fastening holes 140' and formed of a hard material and the outer housing 170 formed of a soft material to closely contact the face of the user are fabricated through double injection molding to form a lateral surface protection frame 500-1. With the configuration as above, the weight of the lateral surface protection frame 500-1 may be minimized, and the structure from double injection molding is implemented by forming the part closely contacting the face with a soft material and forming the part for coupling with a hard material.

By sealing the gap between the eyes and the LCD lenses such that the gap is not open during welding or cutting/grinding, harmful gas and light may be prevented from being introduced through the gap.

Detachment of the lateral surface protection frame 500-1 is facilitated by pulling the escape protrusions, and coupling thereof is performed by fitting the fastening protrusions into the fitting holes. According to this embodiment, the wing surface 190 surrounds portions of the glasses frame other than the upper portion of the glasses frame. The lateral surface protection frame 500-1 is formed by fabricating the inner housing of a hard material and the outer housing 170 of a soft material for close contact with the face of the user through double injection molding.

As such, the lateral surface protection frame is formed at the glasses frame and the weight of the lateral surface protection frame is minimized such that the weight is not concentrated at the front. Thereby, the front and rear portions of the glasses are balanced.

As is apparent from the above description, according to one embodiment of the present invention, safety glasses for blocking of harmful electromagnetic radiation and prevention of dazzling may be designed to have a shape of normal eyeglasses, thus being convenient to use in medical procedures, welding, and cutting/grinding.

In addition, since the nose support is adjustable, the glasses are further convenient to use and wear.

The safety glasses for blocking of harmful electromagnetic radiation according to one embodiment of the present invention are provided with an auxiliary frame to close the gap between the face and the safety glasses created at the bottom and lateral sides of the glasses by a pair of eyeglasses for vision correction or other safety glasses placed in front of the safety glasses in an overlapping manner. Accordingly, the user can safely and conveniently use the safety glasses of the present invention.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. Safety glasses for blocking of harmful electromagnetic radiation comprising:
 a pair of liquid crystal display ("LCD") lenses for blocking of harmful electromagnetic radiation;
 a glasses frame adapted to be worn on a face of a user with the LCD lenses fitted to the left and right sides thereof, the glasses frame being provided with an edge protruding rearward to closely contact the face and an optical sensor for sensing of harmful electromagnetic radiation installed between the LCD lenses; and
 a temple adapted to be hung on ears and joined to both sides of the glasses frame, one side end of the temple being provided with a power supply unit for mounting of a battery and the other side end of the temple being provided with a control switch unit, wherein a circuit wire is installed in the temple to connect the power supply unit to the control switch unit,
 wherein weight of the safety glasses is distributed to a front portion having the LCD lenses and a rear portion having the battery and the control switch unit including a controller such that the safety glasses are balanced when worn by the user,
 wherein the glasses frame comprises a front frame and a rear frame, the LCD lenses being fitted between the front frame and the rear frame and an optical sensor being accommodated and mounted between the front frame and the rear frame,
 wherein a sensing hole allowing the optical sensor to sense the harmful electromagnetic radiation therethrough is formed at a center of the front frame, and an edge of the front frame protrudes rearward; and the rear frame is accommodated in and fastened to an interior of the edge of the front frame, and both sides of a lower portion of a nose support are joined to a center of the rear frame, and
 wherein an elastic segment protruding forward and curved to an upper rear side is formed at an upper portion of the nose support; a multi-stepped interruption step is formed on a curved upper surface of the elastic segment in a front-to-back direction; and a step is formed at a central lower portion of the rear frame such that the interruption step is caught by the step to adjust inclination of the nose support.

2. The safety glasses according to claim 1, wherein the nose support is joined to a center of a rear portion of the glasses frame and placed on a nose of the user, and
 wherein inclination of the nose support is adjusted by pulling or pushing an upper portion of the nose support from or to the glasses frame.

3. The safety glasses according to claim 1, wherein the power supply unit is provided with the battery having a coin shape and a battery cover having a hinge.

4. The safety glasses according to claim 1, further comprising an auxiliary frame coupled to the glasses frame and extending from a lower side and lateral sides of the protruding edge of the glasses frame, the auxiliary frame having an open top.

5. The safety glasses according to claim 1, wherein an inverted L-shaped fitting protrusion protruding rearward is formed at both sides of a rear portion of the nose support;
- a fitting hole allowing the fitting protrusion to be press-fitted thereinto and fixed is formed at both sides of a cushion cover; and
- a push hole is formed in an upper portion of the cushion cover such that an end of the elastic segment is fitted into the push hole and exposed to outside to be pushed by hand.

6. The safety glasses according to claim 1, wherein the control switch unit comprises:
- a welding switch (W) pressed for welding to allow selection of a desired darkening level (level 9, level 10 or level 11) for the welding;
- a cutting/grinding switch (C) pressed for cutting/grinding to allow selection of a desired darkening level (level 5 or level 6) for the cutting/grinding; and
- a sensitivity switch (SE) to adjust sensitivity of response to light intensity on a work site or for intended work to control darkening of the LCD lenses, a level of sensitivity being selected from high (H), middle (M) and low (L) levels according to a work environment.

7. The safety glasses according to claim 1, wherein the control switch unit comprises a remaining battery charge indication lamp, a welding mode switch, a cutting/grinding mode switch, and a sensitivity switch,
wherein welding or cutting/grinding operation is selected from the switches.

8. The safety glasses according to claim 1, wherein a transparent cover provided with a projecting protrusion and an escape protrusion formed on a lateral surface thereof to facilitate installation and detachment of the transparent cover is mounted to a front of the LCD lenses to protect the LCD lenses.

9. The safety glasses according to claim 1, wherein the front frame is provided with an escape groove and a fastening protrusion, and the rear frame is provided with a central fitting groove formed at a center thereof and a side fitting groove formed on each of both left and right sides of the center,
wherein the safety glasses further comprises a lateral surface protection frame,
wherein the lateral surface protection frame comprises an inner housing formed of a hard material and an outer housing formed of a soft material to closely contact the face, the inner housing and the rear housing being fabricated through double injection molding,
wherein the inner housing is provided with a central fitting protrusion, a side fitting protrusion, and a wing surface surrounding a lateral surface of the front frame, the central fitting protrusion and side fitting protrusion being coupled to the fitting grooves,
wherein a lateral surface of the wing surface is provided with a plurality of escape protrusions and fastening holes, each of the escape protrusions and fastening holes being coupled to a corresponding one of the escape groove and fastening protrusion of the front frame, and
wherein the escape protrusions and fastening holes are decoupled from the escape groove and fastening protrusion by pulling the escape protrusions.

10. The safety glasses according to claim 1, wherein the safety glasses are one of medical safety glasses, industrial safety glasses, sport goggle, sunglasses, and fashion glasses.

* * * * *